(12) United States Patent
Habibzadeh

(10) Patent No.: US 12,599,198 B2
(45) Date of Patent: Apr. 14, 2026

(54) ORTHOPEDIC SAFETY BOOT AND ATTACHMENTS COMPLIANT WITH OSHA STANDARDS

(71) Applicant: Alireza Habibzadeh, Tucson, AZ (US)

(72) Inventor: Alireza Habibzadeh, Tucson, AZ (US)

( * ) Notice: Subject to any disclaimer, the term of this patent is extended or adjusted under 35 U.S.C. 154(b) by 18 days.

(21) Appl. No.: 18/779,302

(22) Filed: Jul. 22, 2024

(65) Prior Publication Data

US 2026/0020642 A1     Jan. 22, 2026

(51) Int. Cl.
| | |
|---|---|
| *A43B 7/06* | (2006.01) |
| *A43B 7/32* | (2006.01) |
| *A43B 23/08* | (2006.01) |
| *A61F 5/01* | (2006.01) |
| *A43B 17/16* | (2006.01) |

(52) U.S. Cl.
CPC .............. *A43B 23/086* (2013.01); *A43B 7/06* (2013.01); *A43B 7/32* (2013.01); *A61F 5/0111* (2013.01); *A43B 17/16* (2013.01)

(58) Field of Classification Search
CPC ......... A43B 17/16; A43B 23/086; A43B 7/06; A43B 7/32; A61F 5/058–0585; A61F 5/01–0195; A61B 5/6804; A61B 5/68907
See application file for complete search history.

(56) References Cited

U.S. PATENT DOCUMENTS

| | | | | | |
|---|---|---|---|---|---|
| 2,172,484 | A | * | 9/1939 | Tessier | A61F 5/0585 602/23 |
| 3,618,946 | A | * | 11/1971 | Lee | A43B 5/025 473/438 |
| 3,800,789 | A | * | 4/1974 | Schloss | A61F 5/0585 602/6 |
| 4,083,128 | A | * | 4/1978 | Rossman | A43B 3/26 36/97 |
| 4,177,583 | A | * | 12/1979 | Chapman | A43C 13/14 36/77 R |
| 4,217,893 | A | * | 8/1980 | Payton | A61F 5/0585 602/12 |
| 4,289,122 | A | * | 9/1981 | Mason | A61F 5/0111 602/27 |
| 4,294,238 | A | * | 10/1981 | Woodford | A61F 5/0111 482/79 |
| 4,454,871 | A | * | 6/1984 | Mann | A61F 5/0111 602/27 |
| 4,505,269 | A | * | 3/1985 | Davies | A61F 5/0585 602/27 |

(Continued)

*Primary Examiner* — Katharine G Kane
(74) *Attorney, Agent, or Firm* — Sam Pierce

(57) ABSTRACT

An orthopedic safety attachment for boots comprises a rigid toe cap made of composite material, an attachment means on the interior surface for securing the toe cap to the boot, a flexible outsole with high grip strength properties detachably connected to the toe cap, and an upright portion extending upward to protect the lower leg and ankle. The attachment converts orthopedic boots into OSHA-compliant safety boots. The second embodiment is an orthopedic safety boot comprising a CAM boot with an integrated reinforced toe cap and flexible outsole, providing full compliance with OSHA safety standards. Both embodiments offer enhanced protection and support for individuals recovering from foot injuries, allowing them to safely return to industrial work environments such as warehouses.

15 Claims, 5 Drawing Sheets

(56)     References Cited

U.S. PATENT DOCUMENTS

| | | | | |
|---|---|---|---|---|
| 4,974,583 | A * | 12/1990 | Freitas | A61F 5/0585 |
| | | | | 602/27 |
| 5,142,798 | A * | 9/1992 | Kaufman | A43B 5/047 |
| | | | | 36/117.4 |
| 5,611,156 | A * | 3/1997 | Chiu | A43B 1/0036 |
| | | | | 36/137 |
| 5,926,978 | A * | 7/1999 | Smith | A43B 3/24 |
| | | | | 36/138 |
| 5,954,075 | A * | 9/1999 | Gilmour | A61F 5/0127 |
| | | | | 135/65 |
| 7,134,225 | B2 * | 11/2006 | Ashton | A43B 11/00 |
| | | | | 36/94 |
| 9,603,736 | B1 * | 3/2017 | Buck | A61F 5/0195 |
| 2005/0060914 | A1 * | 3/2005 | Fuerst | B29D 35/122 |
| | | | | 36/102 |
| 2008/0115387 | A1 * | 5/2008 | Walworth | A43B 7/32 |
| | | | | 36/77 R |
| 2011/0185602 | A1 * | 8/2011 | Kurth | A43B 3/0057 |
| | | | | 36/77 R |
| 2014/0223782 | A1 * | 8/2014 | Kuzirian | A43C 11/1493 |
| | | | | 36/107 |
| 2014/0317961 | A1 * | 10/2014 | Mathis | A43B 23/082 |
| | | | | 36/101 |
| 2017/0035150 | A1 * | 2/2017 | Kulp | A43B 23/082 |
| 2018/0177262 | A1 * | 6/2018 | Islas Mares | A43B 3/24 |
| 2019/0116924 | A1 * | 4/2019 | Darby | A43B 13/36 |
| 2019/0254909 | A1 * | 8/2019 | Lee | B25J 9/0006 |
| 2023/0062522 | A1 * | 3/2023 | Kim | A61F 13/043 |
| 2024/0130464 | A1 * | 4/2024 | Gaba | A43B 13/187 |
| 2024/0138521 | A1 * | 5/2024 | Ehring | A43D 11/12 |

* cited by examiner

ORTHOPEDIC SAFETY BOOT AND ATTACHMENTS COMPLIANT WITH OSHA STANDARDS

FIELD OF INVENTION

The present invention relates generally to orthopedic safety footwear and attachments, specifically designed to provide protection and support for individuals recovering from foot injuries while ensuring compliance with OSHA safety standards in industrial environments such as warehouses.

BACKGROUND

Workplace safety and productivity are paramount concerns in industrial sectors, particularly in environments such as construction and manufacturing, where physical demands and occupational hazards are significant. Foot injuries among workers in these industries can lead to substantial disruptions, necessitating the development of solutions that address both the recovery of injured employees and the continuity of their work activities.

Current medical solutions for foot injuries typically involve the use of Controlled Ankle Motion (CAM) boots, which provide support and stability to the injured foot. However, these medical boots lack the necessary safety features, such as reinforced toe caps and high-grip outsoles, required for compliance with Occupational Safety and Health Administration (OSHA) standards in industrial settings. This discrepancy necessitates extended periods of leave for injured workers, resulting in financial strain for both employees, employers, and insurance companies.

The limitations of existing CAM boots, which are not designed to withstand the rigors of industrial environments, exacerbate the problem. Without appropriate safety modifications, these boots fail to protect workers from potential additional injuries, rendering them unsuitable for return-to-work scenarios in hazardous work conditions. Consequently, injured employees are often compelled to remain off work for longer periods, thereby increasing wage replacement costs, reducing productivity, and necessitating the hiring of temporary staff or the payment of overtime to cover their responsibilities.

The inability of current medical boots to meet workplace safety standards also impacts employee morale and overall efficiency. Workers who are unable to return to work promptly due to inadequate safety equipment may experience reduced morale, which can further influence their recovery and reintegration into the workforce. Moreover, the reassignment of tasks to other employees during an injured worker's absence can lead to inefficiencies and slowdowns, affecting overall operational effectiveness.

There is a clear need for an innovative solution that bridges the gap between medical rehabilitation and workplace safety compliance. The development of safety orthopedic boots or boot attachments specifically designed for industrial environments addresses this need. Such solutions ensure that recovering workers can safely resume their duties, thus reducing the duration of their absence and the associated costs. By enabling a quicker return to work, these safety orthopedic solutions offer significant benefits, including cost savings from reduced lost productivity and wage costs, improved employee morale, and sustained workplace efficiency.

In light of these considerations, the impetus for developing a new type of orthopedic boot or boot attachment that meets both medical and OSHA safety standards is evident. This development aims to enhance the rehabilitation process for injured workers while simultaneously addressing the stringent safety requirements of industrial workplaces, thereby providing a comprehensive solution to a prevalent and costly issue.

It is within this context that the present invention is provided.

SUMMARY

The present invention relates to a safety attachment for orthopedic boots, comprising a rigid toe cap, an attachment means, a flexible outsole, and an upright portion. The toe cap is configured to fit over the front portion of an orthopedic boot and is made of a composite material. The flexible outsole, characterized by high grip strength properties, is detachably connected to the toe cap and wraps around the boot to protect the wearer's lower leg and ankle. The invention also includes a kit for converting existing orthopedic boots into safety boots compliant with Occupational Safety and Health Administration (OSHA) standards.

In some embodiments, the composite material of the toe cap includes carbon reinforced polymer, carbon nanotubes, thermoplastic polyamide 66, glass fiber composites, nano carbon, carbon fiber, aluminum, steel, titanium alloy, magnesium alloy, Kevlar-reinforced composites, high-strength polyethylene, thermoplastic polyurethane (TPU), boron carbide, and ceramic composites. These materials provide enhanced durability and protection.

In further embodiments, the attachment means provided on the interior surface of the cavity comprises Velcro, magnetic closure systems, snap-fit mechanisms, adjustable straps, hook and loop fasteners, or zipper closures. These attachment methods offer ease of use and secure fitting of the toe cap to the boot.

In yet further embodiments, the flexible outsole is made of vulcanized rubber, polyurethane, thermoplastic polyurethane (TPU), ethylene vinyl acetate (EVA), extended thermoplastic polyurethane (E-TPU), natural rubber, synthetic rubber, neoprene, silicone rubber, butyl rubber, or nitrile rubber. These materials ensure high grip strength and durability in various industrial environments.

In some embodiments, the upright portion of the outsole includes a handle for ease of application and removal, or adjustable height to cater to different user preferences. This feature facilitates quick and convenient use of the safety attachment.

In further embodiments, the bottom surface of the planar portion of the flexible outsole has a friction coefficient greater than 1.0 and includes a tread pattern to enhance slip resistance. This provides improved stability and safety for the wearer.

In yet further embodiments, the upright portion is configured to extend to a height sufficient to protect the back of the wearer's calf and includes a padded lining for comfort. This design enhances the protective coverage and comfort for the user.

In some embodiments, the first detachable coupling and the second detachable coupling are configured as interlocking clips. This provides a secure and reliable connection between the toe cap and the flexible outsole.

In further embodiments, the safety attachment further comprises a cushioning layer within the internal cavity of the toe cap to enhance comfort, wherein the cushioning layer is made of memory foam, gel inserts, high-density polyethylene foam, shock-absorbing polyurethane foam, or ethylene vinyl acetate (EVA) foam. This cushioning layer adds to the comfort of the wearer.

In yet further embodiments, the flexible outsole includes an embedded shock absorption system and reinforced arch support. These features reduce impact stress on the wearer's foot and provide additional support.

In some embodiments, the toe cap further comprises ventilation holes for breathability and an inner lining for enhanced comfort and fit. These features improve the comfort and wearability of the safety attachment.

In further embodiments, the flexible outsole is characterized by anti-static properties to prevent electric shock. This provides additional safety for the wearer in environments with electrical hazards.

In yet further embodiments, the upright portion further comprises integrated ankle support straps, a detachable protective shin guard, reflective strips for increased visibility, and an integrated heel cup. These features enhance the protective and supportive qualities of the safety attachment.

In some embodiments, the materials used have antimicrobial coatings to prevent odor and infection, and are water-resistant or waterproof. These properties improve hygiene and usability in various conditions.

In further embodiments, the construction includes reinforced stitching for added durability and lightweight construction to reduce fatigue. These features ensure the longevity and comfort of the safety attachment.

The second embodiment of the invention is an orthopedic safety boot comprising a medical Controlled Ankle Motion (CAM) boot with an integrated reinforced toe cap and flexible outsole, compliant with OSHA standards. This embodiment provides the benefits of a complete safety boot solution with integrated protective features.

BRIEF DESCRIPTION OF THE DRAWINGS

Various embodiments of the invention are disclosed in the following detailed description and accompanying drawings.

Figure 1:
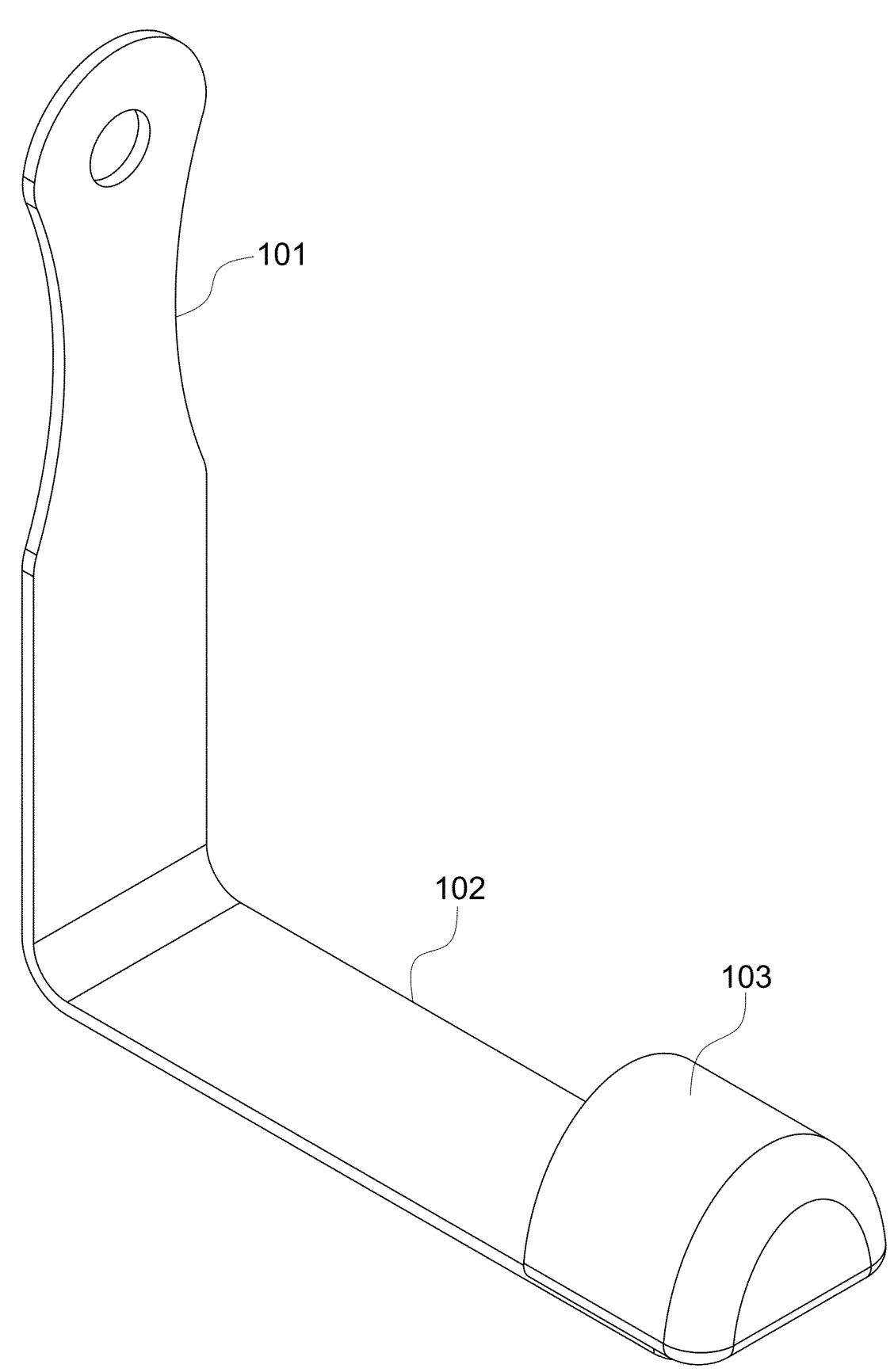
FIG. 1 illustrates an example orthopedic safety attachment showing the upright portion, flexible outsole, and rigid toe cap.

Common reference numerals are used throughout the figures and the detailed description to indicate like elements. One skilled in the art will readily recognize that the above figures are examples and that other architectures, modes of operation, orders of operation, and elements/functions can be provided and implemented without departing from the characteristics and features of the invention, as set forth in the claims.

DETAILED DESCRIPTION AND PREFERRED EMBODIMENT

The following is a detailed description of exemplary embodiments to illustrate the principles of the invention.

The embodiments are provided to illustrate aspects of the invention, but the invention is not limited to any embodiment. The scope of the invention encompasses numerous alternatives, modifications and equivalent; it is limited only by the claims.

Numerous specific details are set forth in the following description in order to provide a thorough understanding of the invention. However, the invention may be practiced according to the claims without some or all of these specific details. For the purpose of clarity, technical material that is known in the technical fields related to the invention has not been described in detail so that the invention is not unnecessarily obscured.

Definitions

The terminology used herein is for the purpose of describing particular embodiments only and is not intended to be limiting of the invention.

As used herein, the term "and/or" includes any combinations of one or more of the associated listed items.

As used herein, the singular forms "a," "an," and "the" are intended to include the plural forms as well as the singular forms, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

When a feature or element is described as being "on" or "directly on" another feature or element, there may or may not be intervening features or elements present. Similarly, when a feature or element is described as being "connected," "attached," or "coupled" to another feature or element, there may or may not be intervening features or elements present. The features and elements described with respect to one embodiment can be applied to other embodiments.

The use of spatial terms, such as "under," "below," "lower," "over," "upper," etc., is used for ease of explanation to describe the relationship between elements when the apparatus is in its proper orientation.

The terms "first," "second," and the like are used to distinguish different elements or features, but these elements or features should not be limited by these terms. A first element or feature described can be referred to as a second element or feature and vice versa without departing from the teachings of the present disclosure.

The term "rigid toe cap" refers to the protective component designed to cover the front portion of an orthopedic boot, providing impact resistance and protection. This includes, but is not limited to, materials such as carbon reinforced polymer, carbon nanotubes, thermoplastic polyamide 66, glass fiber composites, nano carbon, carbon fiber, aluminum, steel, titanium alloy, magnesium alloy, Kevlarreinforced composites, high-strength polyethylene, thermoplastic polyurethane (TPU), boron carbide, and ceramic composites. In one example implementation, the toe cap is made of titanium alloy, providing a balance of strength and lightweight properties.

The term "attachment means" refers to the mechanism used to secure the rigid toe cap to the orthopedic boot. This includes, but is not limited to, Velcro, magnetic closure systems, snap-fit mechanisms, adjustable straps, hook and loop fasteners, and zipper closures. In one example implementation, the attachment means may be a magnetic closure system that allows for quick and secure attachment and detachment of the toe cap to the boot.

The term "flexible outsole" refers to the bottom part of the safety attachment that comes into contact with the ground, providing grip and stability. This includes, but is not limited to, materials such as vulcanized rubber, polyurethane, thermoplastic polyurethane (TPU), ethylene vinyl acetate (EVA), extended thermoplastic polyurethane (E-TPU), natural rubber, synthetic rubber, neoprene, silicone rubber, butyl rubber, and nitrile rubber. In one example implementation, the flexible outsole is made of vulcanized rubber, offering high durability and slip resistance.

The term "upright portion" refers to the part of the flexible outsole that extends upward from the rear of the outsole to wrap around the back of the orthopedic boot, providing additional protection and support to the lower leg and ankle. This includes features such as padded linings, integrated ankle support straps, detachable protective shin guards, reflective strips for increased visibility, and integrated heel cups. In one example implementation, the upright portion includes a padded lining and reflective strips to enhance comfort and visibility.

In some implementations, the rigid toe cap may include ventilation holes for breathability and an inner lining for enhanced comfort and fit. The flexible outsole may feature an embedded shock absorption system and reinforced arch support to reduce impact stress on the wearer's foot. The materials used in the construction of the safety attachment may have anti-microbial coatings to prevent odor and infection, and may be water-resistant or waterproof to ensure usability in various conditions. Reinforced stitching may be used for added durability, and lightweight construction may be employed to reduce fatigue for the wearer.

DESCRIPTION OF DRAWINGS

The present invention relates to an orthopedic safety attachment for boots and an orthopedic safety boot, both designed to address the shortcomings of existing solutions for individuals recovering from foot injuries in industrial environments. The invention specifically aims to provide enhanced protection and support for injured workers, allowing them to safely return to work (for example up to 2 weeks earlier) while ensuring compliance with Occupational Safety and Health Administration (OSHA) safety standards.

Conventional medical boots, such as Controlled Ankle Motion (CAM) boots, are effective in providing the necessary support and stability for foot injuries but lack the safety features required for industrial workplaces. These medical boots are not designed to withstand the hazards present in construction, manufacturing, and other industrial sectors, leading to prolonged absences from work and increased financial strain on both employees and employers. The inability of existing CAM boots to meet workplace safety standards results in extended recovery periods, reduced productivity, and higher costs associated with temporary staffing and overtime.

The present invention overcomes these limitations by introducing a safety attachment that can be retrofitted to existing orthopedic boots, as well as a fully integrated orthopedic safety boot. The safety attachment comprises a rigid toe cap, a flexible outsole, and an upright portion that collectively provide the necessary protection and support to meet OSHA safety standards. The invention allows injured workers to return to work sooner, reducing the need for extended leave and mitigating the financial impact on both employees and employers. By ensuring compliance with safety regulations, the invention enhances worker safety and contributes to maintaining operational efficiency in industrial environments.

The orthopedic safety attachment includes a rigid toe cap made of durable composite materials, providing impact resistance and protection for the front portion of the boot. The flexible outsole, characterized by high grip strength properties, is designed to offer slip resistance and stability, crucial for industrial settings. The upright portion extends upward from the outsole, wrapping around the back of the boot to protect the lower leg and ankle, and includes various features to enhance comfort and usability.

In addition to the safety attachment, the invention encompasses an orthopedic safety boot that integrates these protective features into a single unit. This embodiment provides a comprehensive solution for individuals recovering from foot injuries, ensuring both medical support and industrial safety compliance.

Referring now to the drawings, FIG. 1 illustrates a perspective view of the orthopedic safety attachment for an orthopedic boot. The safety attachment comprises an upright portion (101), a flexible outsole (102), and a rigid toe cap (103). The upright portion (101) is designed to extend upward from the rear of the flexible outsole (102) to wrap around the back of the orthopedic boot, providing additional support and protection to the lower leg and ankle. The upright portion (101) can also act as a handle, facilitating the easy application and removal of the safety attachment. The flexible outsole (102) provides a high-grip surface to enhance stability and slip resistance, while the rigid toe cap (103) protects the front portion of the orthopedic boot from impacts and hazards.

Figure 2:
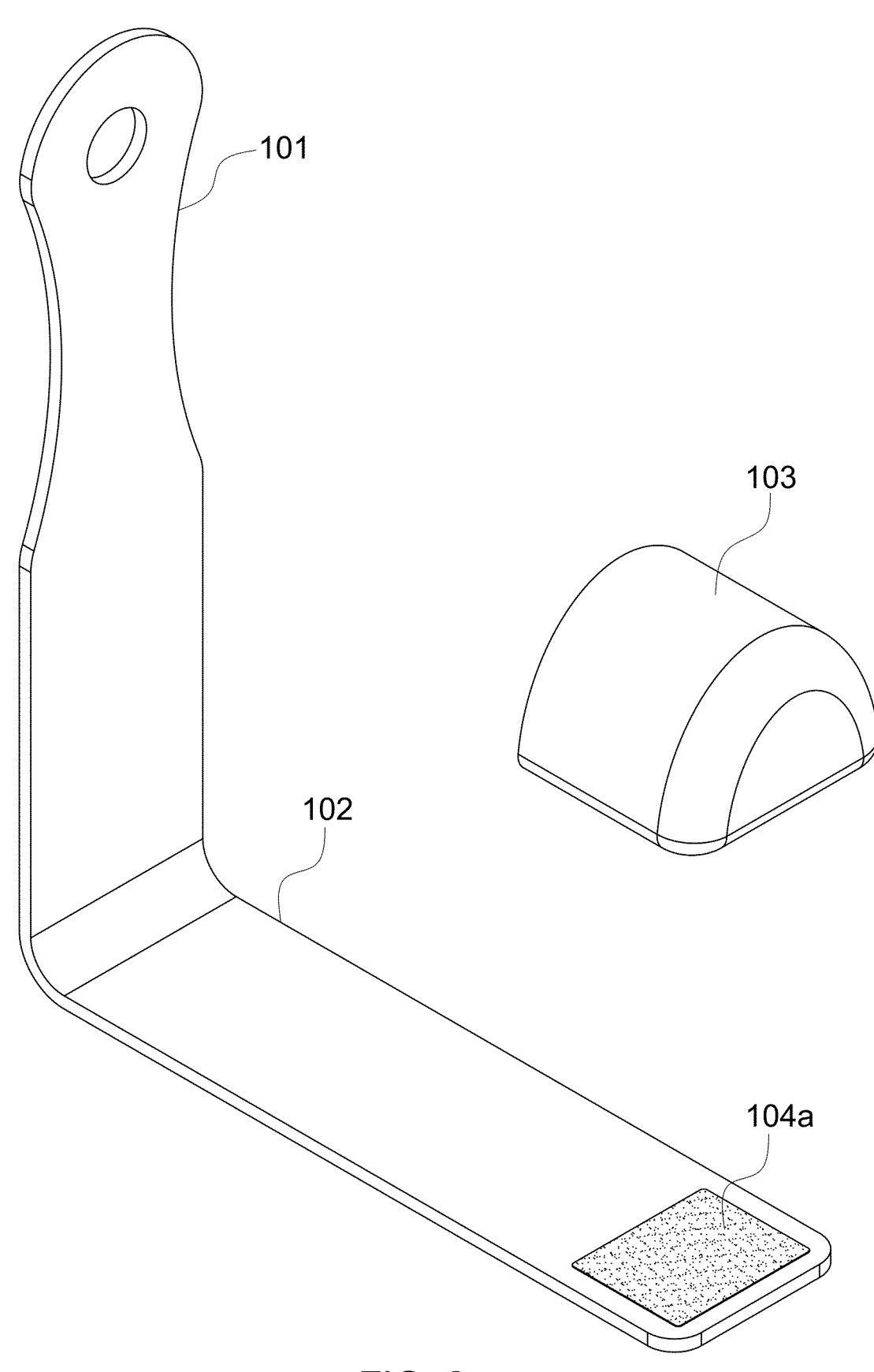
FIG. 2 illustrates an example orthopedic safety attachment with the rigid toe cap detached to show the attachment means on the flexible outsole.

FIG. 2 presents a perspective view of the orthopedic safety attachment with the rigid toe cap (103) detached from the flexible outsole (102). The attachment means (104a) on the flexible outsole (102) are visible in this view. The attachment means (104a) can include various mechanisms such as Velcro, magnetic closures, snap-fit mechanisms, adjustable straps, hook and loop fasteners, or zipper closures. These mechanisms ensure that the rigid toe cap (103) can be securely attached to the flexible outsole (102), providing the necessary protection while allowing for easy attachment and detachment.

Figure 3:
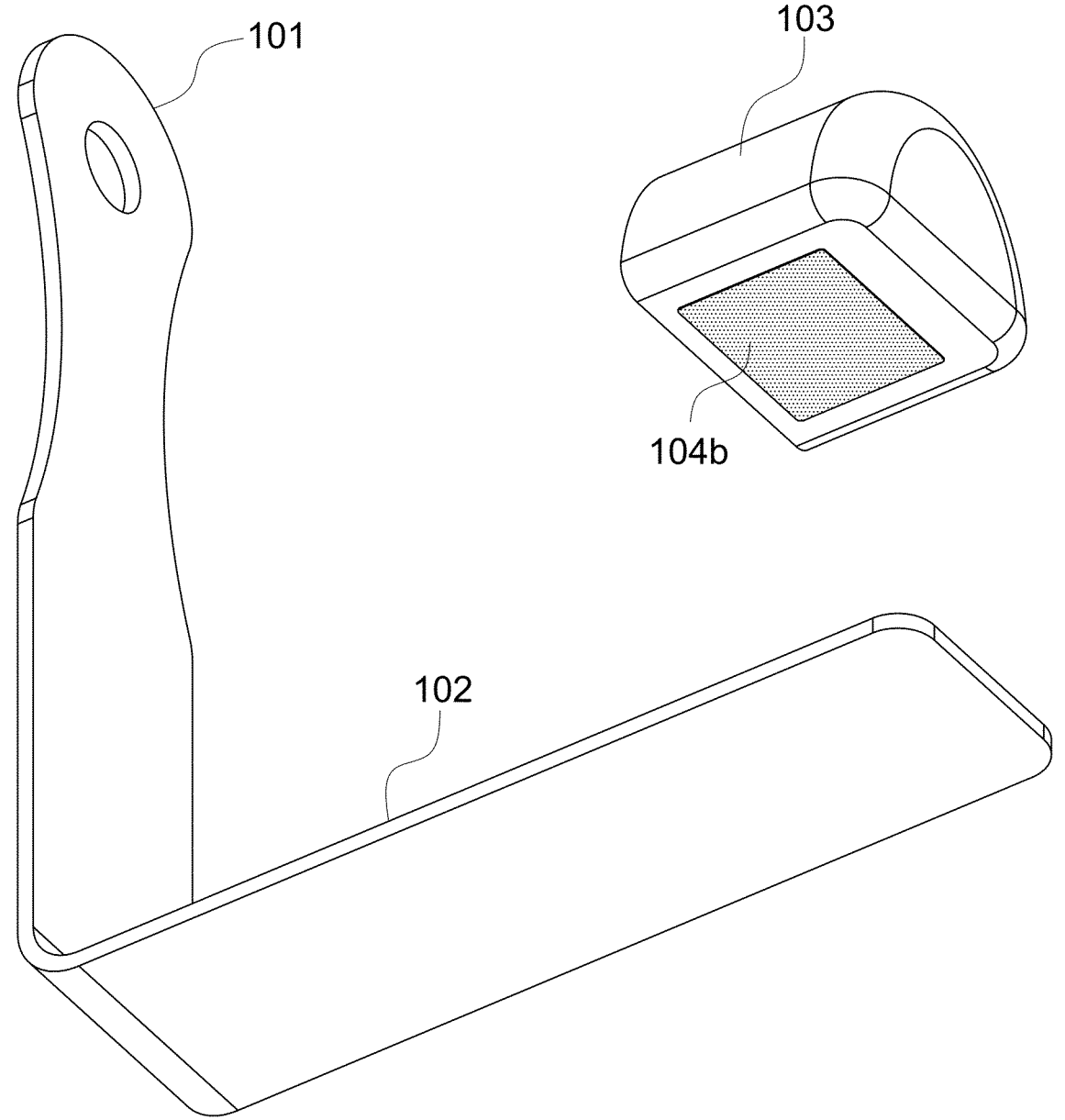
FIG. 3 illustrates an example orthopedic safety attachment highlighting the interior side of the detached rigid toe cap with its attachment means.

FIG. 3 shows another perspective view of the orthopedic safety attachment, highlighting the interior side of the rigid toe cap (103). The attachment means (104b) on the interior surface of the rigid toe cap (103) are shown. The attachment means (104b) are designed to correspond with the attachment means (104a) on the flexible outsole (102) to form a secure connection. The rigid toe cap (103) is made of composite materials such as carbon reinforced polymer, carbon nanotubes, thermoplastic polyamide 66, glass fiber composites, nano carbon, carbon fiber, aluminum, steel, titanium alloy, magnesium alloy, Kevlar-reinforced composites, high-strength polyethylene, thermoplastic polyurethane (TPU), boron carbide, or ceramic composites. These materials provide the necessary impact resistance and durability.

Figure 4A:
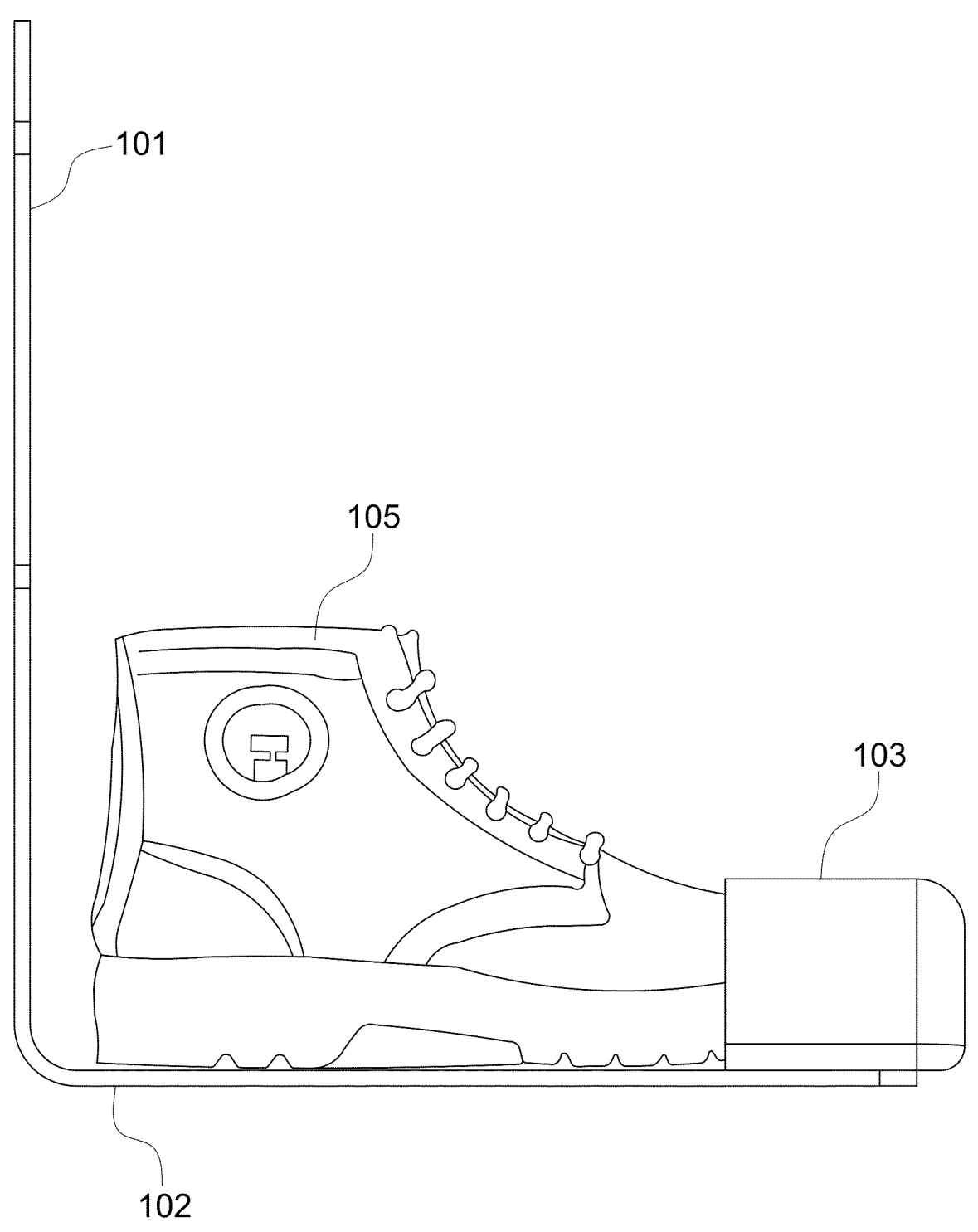
FIG. 4A illustrates an example orthopedic safety attachment fitted onto an orthopedic boot with the upright portion wrapping around the back of the boot.

FIG. 4A illustrates a side view of the orthopedic safety attachment fitted onto an orthopedic boot (105). The upright portion (101) is shown extending upward from the rear of the flexible outsole (102) to wrap around the back of the orthopedic boot (105). This configuration provides additional protection and support to the wearer's lower leg and ankle. The upright portion (101) also acts as a handle, making it easier for the user to apply and remove the attachment. The flexible outsole (102) is characterized by high grip strength properties and may include a tread pattern to enhance slip resistance. The rigid toe cap (103) is positioned at the front of the orthopedic boot (105), protecting the front portion from impacts.

Figure 4B:
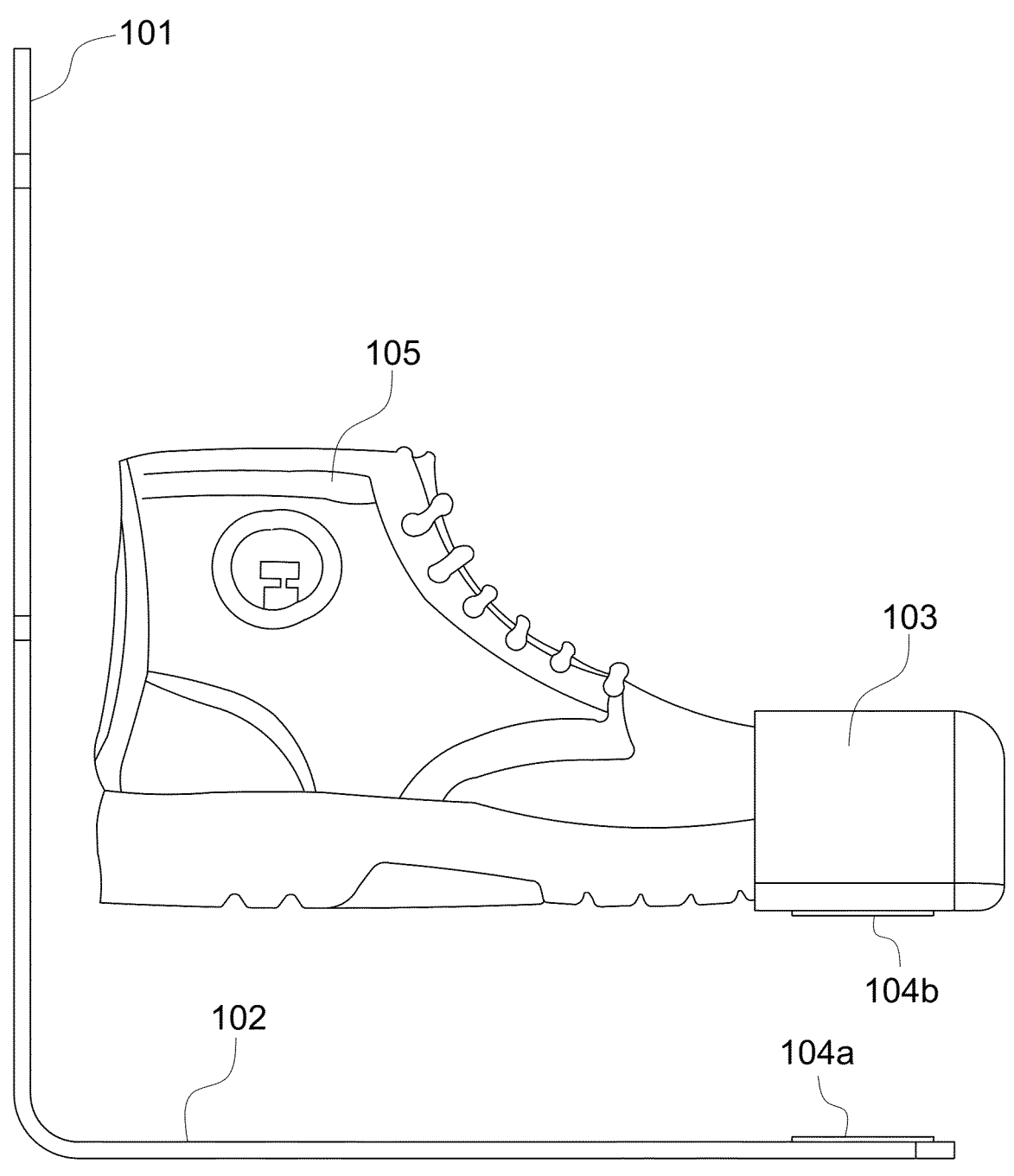
FIG. 4B illustrates an example orthopedic safety attachment with the flexible outsole and rigid toe cap detached, showing the attachment means and a separate orthopedic boot.

FIG. 4B shows a side view similar to FIG. 4A, but with the flexible outsole (102) and rigid toe cap (103) detached from the orthopedic boot (105). The attachment means (104a) on the flexible outsole (102) and the corresponding attachment means (104b) on the rigid toe cap (103) are visible. This view demonstrates how the rigid toe cap (103) can be detached from the flexible outsole (102), allowing for easy removal and replacement. The orthopedic boot (105) is shown separately, highlighting how the safety attachment can be fitted onto an existing orthopedic boot to convert it into an OSHA-compliant safety boot.

The orthopedic safety attachment may include additional features to enhance comfort and usability. For example, the upright portion (101) may include a padded lining for added comfort, and reflective strips for increased visibility. The flexible outsole (102) may have an embedded shock absorption system and reinforced arch support to reduce impact stress on the wearer's foot. The rigid toe cap (103) may include ventilation holes for breathability and an inner lining for enhanced comfort and fit. The materials used in the construction of the safety attachment may have anti-micro-bial coatings to prevent odor and infection, and may be water-resistant or waterproof to ensure usability in various conditions. Reinforced stitching may be used for added durability, and lightweight construction may be employed to reduce fatigue for the wearer.

In the second embodiment of the invention, the features of the orthopedic safety attachment described in FIGS. 1 through 4B are integrated directly into the structure of a medical Controlled Ankle Motion (CAM) boot. This integration provides a unified, comprehensive solution that combines the medical support of a CAM boot with the safety features required for compliance with Occupational Safety and Health Administration (OSHA) standards.

The medical CAM boot in this embodiment incorporates a rigid toe cap, similar to the toe cap (103) shown in the figures for the first embodiment. The toe cap is made from composite materials such as carbon reinforced polymer, carbon nanotubes, thermoplastic polyamide 66, glass fiber composites, nano carbon, carbon fiber, aluminum, steel, titanium alloy, magnesium alloy, Kevlar-reinforced compos-ites, high-strength polyethylene, thermoplastic polyurethane (TPU), boron carbide, or ceramic composites. These mate-rials ensure that the toe cap provides robust impact resis-tance and protection for the front portion of the boot.

The flexible outsole, analogous to the flexible outsole (102) described in the first embodiment, is permanently integrated into the bottom of the CAM boot. This outsole is constructed from materials such as vulcanized rubber, poly-urethane, thermoplastic polyurethane (TPU), ethylene vinyl acetate (EVA), extended thermoplastic polyurethane (E-TPU), natural rubber, synthetic rubber, neoprene, silicone rubber, butyl rubber, or nitrile rubber. The flexible outsole features high grip strength properties, possibly including a tread pattern to enhance slip resistance and stability, making it suitable for various industrial environments.

The upright portion, which in the first embodiment is a separate component (101), is integrated into the rear and sides of the CAM boot. This portion extends upward to wrap around the wearer's lower leg and ankle, providing addi-tional support and protection. Similar to the first embodi-ment, this integrated upright portion can include a padded lining for comfort, reflective strips for increased visibility, and integrated ankle support straps. It may also feature a detachable protective shin guard and an integrated heel cup to enhance stability.

Additional features present in the first embodiment are similarly incorporated into the second embodiment. The boot may include a cushioning layer within the interior, providing enhanced comfort. This cushioning layer can be made from materials such as memory foam, gel inserts, high-density polyethylene foam, shock-absorbing polyure-thane foam, or ethylene vinyl acetate (EVA) foam. Ventila-tion holes may be incorporated into the boot's structure to ensure breathability, while an inner lining improves fit and comfort.

The second embodiment also benefits from the same material properties as the first, such as anti-microbial coat-ings to prevent odor and infection, and water-resistant or waterproof materials to ensure usability in various condi-tions. Reinforced stitching and lightweight construction enhance durability and reduce wearer fatigue.

By integrating these safety features directly into the structure of a medical CAM boot, the second embodiment provides a cohesive and practical solution for individuals recovering from foot injuries. This design allows workers to return to their industrial roles more quickly and safely, maintaining compliance with OSHA standards without the need for additional attachments or modifications. This embodiment offers the dual benefits of medical support and workplace safety in a single, unified product.

CONCLUSION

Unless otherwise defined, all terms (including technical terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

The disclosed embodiments are illustrative, not restric-tive. While specific configurations of the attachments and safety boot of the invention have been described in a specific manner referring to the illustrated embodiments, it is under-stood that the present invention can be applied to a wide variety of solutions which fit within the scope and spirit of the claims. There are many alternative ways of implement-ing the invention.

It is to be understood that the embodiments of the inven-tion herein described are merely illustrative of the applica-tion of the principles of the invention. Reference herein to details of the illustrated embodiments is not intended to limit the scope of the claims, which themselves recite those features regarded as essential to the invention.

What is claimed is:

1. A safety attachment for an orthopedic boot, comprising consisting of:

a rigid toe cap configured to form an internal cavity to fit over the front portion of an orthopedic boot, the toe cap being made of a composite material;

an attachment means provided on the interior surface of the cavity for securing the toe cap to the orthopedic boot;

a flexible outsole having a planar portion with a bottom surface characterized by high grip strength properties and an upper surface, wherein the upper surface of the flexible outsole is a solid unobstructed flat surface and free of holes and obstructions from the heel end to attachment means provided at the toe end on the top of the flexible outsole; and an upright portion coupled to the planar portion at an opposing second end, the upright portion being a solid unobstructed flat surface, solidify and free of holes or obstructions extending upward to wrap around the back of the orthopedic boot to protect the wearer's lower leg and ankle and including an aperture, wherein:

wherein:

the toe cap is configured to be secured to an orthopedic boot prior to the orthopedic boot being joined with the safety attachment; and attachment means provided on the bottom of the toe cap is configured to detachably join with the attachment means provided at the toe end on the top of the flexible outsole.

2. The safety attachment of claim 1, wherein the composite material of the toe cap is selected from the group consisting of carbon reinforced polymer, carbon nanotubes, thermoplastic polyamide 66, glass fiber composites, nano carbon, carbon fiber, aluminum, steel, titanium alloy, magnesium alloy, Kevlar-reinforced composites, high-strength polyethylene, thermoplastic polyurethane (TPU), boron carbide, and ceramic composites.

3. The safety attachment of claim 1, wherein the attachment means provided on the interior surface of the cavity comprises Velcro, magnetic closure system, snap-fit mechanism, adjustable straps, hook and loop fasteners, or zipper closure.

4. The safety attachment of claim 1, wherein the flexible outsole is made of a material selected from the group consisting of vulcanized rubber, polyurethane, thermoplastic polyurethane (TPU), ethylene vinyl acetate (EVA), extended thermoplastic polyurethane (E-TPU), natural rubber, synthetic rubber, neoprene, silicone rubber, butyl rubber, and nitrile rubber.

5. The safety attachment of claim 1, wherein the upright portion of the outsole includes a handle for ease of application and removal, or adjustable height to cater to different user preferences.

6. The safety attachment of claim 1, wherein the bottom surface of the planar portion of the flexible outsole has a friction coefficient greater than 1.0, and includes a tread pattern to enhance slip resistance.

7. The safety attachment of claim 1, wherein the upright portion is configured to extend to a height sufficient to protect the back of the wearer's calf, and includes a padded lining for comfort.

8. The safety attachment of claim 1, wherein the first detachable coupling and the second detachable coupling are configured as interlocking clips.

9. The safety attachment of claim 1, further comprising a cushioning layer within the internal cavity of the toe cap to enhance comfort, wherein the cushioning layer is made of memory foam, gel inserts, high-density polyethylene foam, shock-absorbing polyurethane foam, or ethylene vinyl acetate (EVA) foam.

10. The safety attachment of claim 1, wherein the flexible outsole further includes an embedded shock absorption system and reinforced arch support.

11. The safety attachment of claim 1, wherein the toe cap further comprises ventilation holes for breathability and an inner lining for enhanced comfort and fit.

12. The safety attachment of claim 1, wherein the flexible outsole is characterized by anti-static properties to prevent electric shock.

13. The safety attachment of claim 1, wherein the upright portion further comprises integrated ankle support straps, a detachable protective shin guard, reflective strips for increased visibility, and an integrated heel cup for enhanced stability.

14. The safety attachment of claim 1, wherein the materials used have anti-microbial coatings to prevent odor and infection, and are water-resistant or waterproof.

15. The safety attachment of claim 1, wherein the construction includes reinforced stitching for added durability and lightweight construction to reduce fatigue.

* * * * *